United States Patent [19]

Miles et al.

[11] Patent Number: 5,135,304
[45] Date of Patent: Aug. 4, 1992

[54] GAS ANALYSIS SYSTEM HAVING BUFFER GAS INPUTS TO PROTECT ASSOCIATED OPTICAL ELEMENTS

[75] Inventors: Scott D. Miles, Sandy; John R. Mitchell, Salt Lake City; Donald E. Gregonis, Salt Lake City; Joel M. Harris, Salt Lake City, all of Utah

[73] Assignee: BOC Health Care, Inc., Murray Hill, N.J.

[21] Appl. No.: 771,625

[22] Filed: Oct. 4, 1991

Related U.S. Application Data

[63] Continuation-in-part of Ser. No. 522,533, May 11, 1990.

[51] Int. Cl.$^5$ .......................... G01J 3/44; G01N 21/65
[52] U.S. Cl. .................... 356/301; 356/338; 356/246; 250/576
[58] Field of Search ............... 356/301, 338, 339, 343, 356/244, 246, 437, 438, 439, 440; 250/573, 574, 576; 359/509

[56] References Cited

U.S. PATENT DOCUMENTS

| | | | |
|---|---|---|---|
| 3,515,482 | 6/1970 | Garrow et al. | 356/439 |
| 3,833,305 | 9/1974 | Porter et al. | |
| 4,071,298 | 1/1978 | Falconer | 356/338 |
| 4,113,386 | 9/1978 | Lepper, Jr. | 356/338 |
| 4,225,243 | 9/1980 | Typpo | 356/439 |
| 4,277,131 | 7/1981 | Hart et al. | 356/439 |
| 4,413,911 | 11/1983 | Rice et al. | 356/438 |
| 4,443,072 | 4/1984 | Ballard | 356/246 |
| 4,515,274 | 5/1985 | Hollinger et al. | 356/246 |
| 4,544,273 | 10/1985 | Berndt | 356/437 |
| 4,594,715 | 6/1986 | Knollenberg | |
| 4,647,780 | 3/1987 | Dunkel | 356/438 |
| 4,648,714 | 3/1987 | Benner et al. | 356/301 |
| 4,649,830 | 3/1987 | Tanaka | |
| 4,654,226 | 3/1987 | Jackson et al. | |
| 4,672,620 | 6/1987 | Slusher et al. | |
| 4,676,639 | 6/1987 | Van Wagenen | 356/246 |
| 4,701,096 | 10/1987 | Fisher, Jr. | |
| 4,713,964 | 12/1987 | Ioannides | 356/439 |
| 4,723,063 | 2/1988 | Armier et al. | |
| 4,746,215 | 5/1988 | Gross | 356/339 |
| 4,784,486 | 11/1988 | Van Wagenen et al. | 356/301 |
| 4,784,491 | 11/1988 | Penney et al. | 356/376 |
| 4,786,188 | 11/1988 | Myhre et al. | |
| 4,787,750 | 11/1988 | Nelson et al. | 356/437 |
| 4,837,443 | 6/1989 | Young et al. | |
| 4,840,226 | 6/1989 | Richlen | |
| 4,845,426 | 7/1989 | Nolan et al. | |
| 4,846,102 | 7/1989 | Ozias | |
| 4,924,097 | 5/1990 | Browner et al. | 356/301 |
| 4,940,327 | 7/1990 | Lilienfeld | 356/338 |
| 4,983,038 | 1/1991 | Ohki et al. | 356/246 |
| 5,011,286 | 4/1991 | Petralli | 356/338 |

FOREIGN PATENT DOCUMENTS

| | | | |
|---|---|---|---|
| 2061491 | 6/1971 | France | |
| 2210291 | 7/1974 | France | |
| 60-233536 | 11/1985 | Japan | 356/439 |
| 1376011 | 2/1988 | U.S.S.R. | 356/246 |

Primary Examiner—F. L. Evans
Attorney, Agent, or Firm—Dennis Epperson; Roger M. Rathbun; Larry R. Cassett

[57] ABSTRACT

A gas analysis cell positioned within an optical resonant cavity in a gas analysis system is disclosed wherein the cell includes a flow of buffer gas which forms a "dam", thereby protecting the optical elements in the analysis system. The analysis cell includes an inlet for introducing a gas sample into the analysis chamber of the cell. Two buffer gas inlet ports, one on each end of the cell, are provided to introduce a flow of buffer gas which is directed past optical elements in the system adjacent the ends of the cell. Two output ports are located at the ends of the analysis chamber to remove the buffer gas and gas sample mixture. The flow of buffer gas acts to confine the gas sample within the analysis chamber and reduce adverse effects which occur when the gas sample comes in contact with the optical elements of the system. By providing a constant non-turbulent flow of gas adjacent the system optics, adverse changes in index of refraction are avoided, thus reducing beam steering and Schlieren effects which can occur when Brewster windows or other optics are used to constrain the gas sample within the analysis cell. The buffer gas flow in the analysis cell of the present invention eliminates the need for gas cell windows which have intrinsic losses. This in turn minimizes losses which cause lower circulating intracavity power and signal strength.

28 Claims, 4 Drawing Sheets

GAS ANALYSIS SYSTEM HAVING BUFFER GAS INPUTS TO PROTECT ASSOCIATED OPTICAL ELEMENTS

RELATED APPLICATION

This application is a continuation-in-part of patent application Ser. No. 522,533, filed May 11, 1990, by inventor Scott Miles, and entitled "Gas Analysis System Having Buffer Gas Inputs To Protect Associated Optical Elements".

FIELD OF THE INVENTION

The invention relates to a gas analysis cell, and, in particular, to a gas analysis cell for containing a gas sample in a laser Raman gas analysis system.

BACKGROUND OF THE INVENTION

Raman light scattering has been successfully used in critical care situations to continuously monitor a patient's respiratory gases. This technique is based on the effect which occurs when monochromatic light interacts with vibrational/rotational modes of gas molecules to produce scattered light which is frequency shifted from that of the incident radiation by an amount corresponding to the vibrational/rotational energies of the scattering gas molecules. If the incident light photon loses energy in the collision, it is re-emitted as scattered light with lower energy and consequently lower frequency than the incident photon. In a similar manner, if the incident photon gains energy in the collision, it is re-emitted as scattered light with higher energy and higher frequency than the incident photon. Since these energy shifts are species-specific, analysis of the various frequency components present in the Raman scattering spectrum of a sample provides chemical identification of the gases present in the scattering volume. The intensity of the various frequency components or Raman spectral lines provides quantification of the gases present, providing suitable calibrations have been made. In this manner, Raman light scattering can be employed to determine the identity and quantity of various respiratory and anesthetic gases present in a patient's breath in operating room and intensive care situations.

In addition to critical care situations, Raman light scattering gas analysis can also be used in many industrial applications such as stack gas analysis for combustion control, process control, fermentation monitoring, and pipeline gas mixture control. This analysis technique can also be extended to meet environmental monitoring needs in many areas such as escaped anesthetic agents in the operating room, air pollution, auto emissions testing and submarine atmosphere monitoring.

Systems developed for analysis of gases in critical care situations utilizing Raman scattering typically employ gas cells which contain a sample of the patient's respiratory gas to be analyzed. The gas sampling cell is located either within the resonant cavity of a laser or outside the cavity. In an intracavity system, a laser beam is directed through the resonant cavity such that it intercepts the gas within the sampling cell. Raman scattered light from the gas analysis region within the cell is collected by a collection optic and directed through one or more interference filters. The collection optics and interference filters and possibly focusing optics in turn transmit the Raman scattered light to appropriate detectors for quantitating each specific Raman signal, and thus, each specific gas comprising the respiratory sample.

Windows are commonly provided on either end of the gas sampling cell to protect surrounding optical elements and filters from contaminants which may be present in the gas sample. The windows further serve to confine the gas sample within the chamber, minimizing the volume of the sample and thus improving response time. In some systems, the gas cell windows can be oriented at Brewster's angle to select and improve the transmission of a particular polarization of light passing through the sample. In this manner, optical losses in the laser beam which passes through the cell are minimized. However, the gas sample, in combination with particulates often carried with the sample, contaminates the cell windows and degrades the performance of the system. For example, this contamination may result in undesirable light scattering, and thus, the electrical power, and correspondingly, the laser current, required to maintain the laser light intensity is greatly increased. If untreated and uncorrected, the system will cease to function properly. Current respiratory gas analysis systems require periodic replacement or cleaning of the gas cell to compensate for the accumulation of contaminants. This is generally a time-consuming process which involves not only the replacement or cleaning of the cell, but also, recalibration of the system, both at substantial expense in both time and money.

An improved apparatus for confining a gas sample within an analysis region can be provided by removing the windows from the ends of the gas sampling cell and forming air dams or curtains of air between the sample gases and the optical elements at the surrounding optical elements. Such a system is described in commonly assigned copending application Ser. No. 522,533. These systems are quite adequate in applications where the index of refraction of the sample gases does not change. However, in applications where the index of refraction of the sample gases is variable, it is often difficult to maintain optimum laser power in the resonant cavity. This is because index of refraction differences can cause laser beam movement and alignment changes, which affect the optical characteristics of the resonant cavity as well as the detection optics. In cases where the changes in index of refraction are predictable or known, it is possible to compensate by an appropriate calibration procedure. However, in many applications these changes are not predictable or known. For example, in a respiratory gas analysis system, the index of refraction of the gases being drawn into the gas cell changes with each breath taken by the patient.

When the laser beam passes through the interfacial regions or interfaces P and P' (shown in FIG. 4) formed between the air dam buffer gas and the gas being analyzed in the gas cell, it is "steered" by that interfacial region between the gases to a greater or lesser extent (as shown in FIG. 4). The extent to which the beam is "steered" is dependent on at least two things: 1) the difference between the refractive index of the analyte gas in the analysis portion of the gas cell ($n_A$) and the refractive index of the air dam buffer gas ($n_B$); and 2) the angles formed by the intersection of the laser beam axis with the interfacial regions P and P'.

The composition, and thus the index of refraction ($n_B$), of the air dam buffer gas does not normally change during use. However, the index of refraction ($n_A$) of the analyte gas mixture inside the gas cell often changes as the makeup of that gas changes. For example, in medical applications, the index of refraction of the gas/agent mixture changes appreciably when the gas in the gas cell changes from simple room air to a mixture with a high concentration of Nitrous Oxide. Furthermore, if the gas/agent mixture comprises respiratory gases from a patient, the index of refraction of the sample gas changes as the patient inhales and exhales.

At least two significant problems can occur when these index of refraction changes/beam steering effects occur. First, when the gas composition changes, the index of refraction changes, and therefore the path of the laser beam through the resonant cavity is altered. When the beam path changes, it changes the location at which the beam reflects off the mirror at the other end of the resonator. When this alignment change occurs, the lasing efficiency can drop significantly, thus causing loss in laser power which in turn causes the intensity of the Raman scattered light going to the detectors to drop. This loss of Raman signal reduces the signal to noise ratio of the system and is therefore undesirable. Secondly, when the path of the laser beam through the gas analysis cell changes, it may cause the laser beam to move out of the location which optimizes the efficiency of the detector system. The Raman scattered light which is coming from the laser beam and being focused on the detectors is used to identify and quantify the analyte gases. A shift of the laser beam location relative to the detector system changes the amount of light falling on the detectors and therefore changes the measurements being made in unpredictable ways. The present invention dramatically reduces these undesirable effects caused by varying gas composition and fluctuations in the index of refraction of the gases in the gas analysis cell.

SUMMARY OF THE INVENTION

In accordance with one embodiment of the present invention, a gas analysis cell is located within the resonant cavity of a laser in a gas analysis system. The ends of the resonant cavity are defined by two reflectors, preferably in the form of high reflectivity mirrors, gratings, or other known reflective elements. A sample of the gas to be analyzed is admitted to an analysis chamber within the analysis cell and a laser beam is directed through the analysis chamber such that the beam intercepts the gas sample therein. Raman scattered light is collected in detector channels adjacent the analysis chamber and analyzed with signal processing means in order to determine the type and quantity of the various gases comprising the sample.

The gas analysis cell of the present invention includes in addition to a sample input port, two input ports through which a flow of buffer gas is introduced. The flow of buffer gas is directed past optical elements on either end of the analysis cell. Two output ports are located on the ends of the analysis chamber to remove both the buffer gas and gas sample. The buffer gas flow acts to effectively confine the sample gas within the analysis region of the chamber and prevents the gas sample from contacting and contaminating the mirrors and any other optical elements in the cavity. Since no exposure of the optical elements to the gas sample occurs, the detrimental effects of the sampled gas upon the system optics are prevented. In addition, the constant, nonturbulent flow of buffer gas reduces the variation in density gradients of the gas flow within the gas cell, thereby reducing adverse effects such as beam steering and Schlieren effects which result from abrupt changes in refractive index caused by varying density gradients in the gas flow along the optical path of the light beam.

The present invention provides a gas analysis system comprising a cavity having an optical element wherein the cavity is capable of propagating a beam of optical radiation. A gas cell is positioned within the cavity and adapted to receive a gas sample. The gas cell is further configured to permit the beam to pass through the gas sample. A buffer gas inlet port is coupled to the cavity for introducing a flow of buffer gas to the cavity wherein the flow of buffer gas substantially prevents the gas sample from contacting the optical element. The cavity may be a resonant cavity. In addition, the resonant cavity may be a lasing cavity adapted for the amplification of light. The gas cell may further comprise at least one light output channel for transporting light which is scattered out of the beam of optical radiation by the gas sample. The analysis system may also include an outlet port coupled to the resonant cavity for removing gases from the gas cell and the cavity. The buffer gas inlet port may be constructed and arranged so that buffer gas floods a region adjacent the optical element. Also, the buffer gas inlet port may be constructed and arranged so that the flow of buffer gas into the cavity is non-turbulent.

An apparatus for the analysis of a gas sample is disclosed comprising a laser light source for producing a laser beam. The laser source comprises a resonant cavity and a lasing medium located within the resonant cavity. A gas cell is positioned within the resonant cavity. The gas cell comprises a housing and an analysis chamber enclosed within the housing. A sample gas inlet port is formed in the housing for introducing a gas sample into the analysis chamber and a buffer gas inlet port is formed in the housing for receiving a flow of buffer gas. A gas outlet port is formed in the housing wherein the outlet port provides an outlet for the buffer gas and the gas sample in a manner which substantially confines the sample gas to a region of the analysis chamber located intermediate the sample gas inlet port and the gas outlet port. The analysis chamber may further comprise at least one light output channel for transporting light which is scattered out of the laser beam by the gas sample.

In accordance with the present invention, a gas analysis system is disclosed comprising a laser having a longitudinal resonant cavity wherein the ends of the cavity are defined by first and second high reflectivity mirrors. A gas analysis cell is positioned within the resonant cavity intermediate the mirrors and comprises an analysis chamber having a first end and a second end. A sample gas inlet port is located intermediate the analysis chamber first and second ends for introducing a gas sample into the analysis chamber. First and second buffer gas inlet ports are located at the first and second ends of the analysis chamber for introducing a flow of buffer gas into the analysis cell. First and second outlet ports are located near the first and second ends of the analysis chamber for removing the gases from the analysis cell such that the flow of buffer gas between the buffer gas inlet ports and the outlet ports confines the gas sample to the analysis chamber.

A method for constraining a gas sample within a gas analysis cell located within a cavity is disclosed comprising the steps of introducing the gas sample into the analysis cell and introducing a flow of buffer gas into the analysis cell such that the flow of buffer gas through the cell substantially confines the gas sample within the analysis cell.

The present invention provides a device for the analysis of gases in a gas sample utilizing Raman light scattering comprising an optical cavity and a gas analysis chamber for receiving a gas sample. The chamber is positioned within the optical cavity and in fluid communication with at least a portion of the cavity located outside the analysis chamber. The device may further comprise a gas dam for substantially constraining the gas sample to the analysis chamber.

In one embodiment, the present invention comprises a resonant cavity for propagating a beam of optical radiation; and a gas cell positioned within the resonant cavity which is adapted to receive a gas sample in an analysis chamber having an optical axis. The gas cell further comprises a first buffer gas chamber adjacent a first end of the analysis chamber and a second buffer gas chamber adjacent a second end of the analysis chamber. The cell is configured to permit the beam of optical radiation to enter and exit the analysis chamber through the first and second buffer gas chambers. A first mixed gas outlet port is located intermediate the gas analysis chamber and the first buffer gas chamber, wherein sample gases from the analysis chamber mix with buffer gases from the first buffer gas chamber to form a first air dam having a first set of optical characteristics. A second mixed gas outlet port is located intermediate the gas analysis chamber and the second buffer gas chamber, wherein sample gases from the analysis chamber mix with buffer gases from the second buffer gas chamber to form a second air dam having a second set of optical characteristics. The second set of optical characteristics are substantially the reciprocal of the first set of optical characteristics so that any steering effects on the beam of optical radiation caused by propagating the beam through the first air dam are substantially reversed so as to counteract the steering effects upon propagation of the beam through the second air dam.

The invention may further comprise a detector channel having an optical axis, wherein the detector channel optical axis and the analysis chamber optical axis define a first plane through the analysis chamber. Additionally, the first plane may intersect a portion of the first and/or second mixed gas outlet ports. The invention may also have the first mixed gas outlet port and the second mixed gas outlet port located on opposite sides of the analysis chamber optical axis.

In certain embodiments, the air dam of the present invention further comprises an interfacial region formed by the sample gases in the analysis chamber and the buffer gases in the first buffer gas chamber. The interfacial region may be planar and form an angle with respect to the analysis chamber optical axis. In some embodiments, the interfacial region is substantially perpendicular to the analysis chamber optical axis.

In another embodiment, the first air dam further comprises a region intermediate the sample gases in the analysis chamber and the buffer gases in the first buffer gas chamber, wherein the region has an index of refraction profile which is a function of the indices of refraction of the gas sample and the buffer gas.

In another embodiment, the gas analysis system of the present invention comprises a resonant cavity for propagating a beam of optical radiation; and a gas cell positioned within the resonant cavity. The gas cell comprises an analysis chamber having an optical axis; an inlet port for introducing a gas sample into the analysis chamber; and a first air dam adjacent a first end of the analysis chamber and a second air dam adjacent a second end of the analysis chamber for confining the sample gas within the analysis chamber. The beam of optical radiation can enter and exit the analysis chamber through the first and second air dams and the first and second air dams have optical characteristics which are substantially the reciprocal of each other so that any steering of the beam of optical radiation caused by propagating through the first air dam is substantially counteracted upon propagation of the beam through the second air dam.

In some embodiments of the invention, the first air dam further comprises a region intermediate the sample gases in the analysis chamber and a buffer gas in a first buffer gas chamber. The region has an index of refraction profile which is a function of the indices of refraction of the gas sample and the buffer gas.

One embodiment of the invention comprises a gas cell having an analysis chamber with a sample gas inlet port and an optical axis; a detector channel having an optical axis, wherein the detector channel optical axis and the analysis chamber optical axis define a first plane through the analysis chamber; a first buffer chamber in fluid communication with a first end region of the analysis chamber; a second buffer chamber in fluid communication with a second end region of the analysis chamber; a first gas outlet port located intermediate the sample gas inlet port and the first buffer chamber for removing gases from the analysis chamber and the first buffer chamber thereby forming a first mixed gas interfacial region between the analysis chamber and the first buffer chamber, wherein the first plane intersects a portion of the first gas outlet port: and a second gas outlet port located intermediate the sample gas inlet port and the second buffer chamber for removing gases from the analysis chamber and the second buffer chamber thereby forming a second mixed gas interfacial region between the analysis chamber and the second buffer chamber, wherein the first plane intersects a portion of the second gas outlet port and the first and second gas outlet ports are located on opposite sides of the analysis chamber optical axis.

In this embodiment, the first and second mixed gas interfacial regions may further have optical properties which are substantially the reciprocal of each other so that any steering of a beam of optical radiation propagating from the first buffer chamber through the first mixed gas interfacial region into the analysis chamber is substantially counteracted upon propagation of the beam of optical radiation propagating from the analysis chamber through the second mixed gas interfacial region into the second buffer chamber.

In yet another embodiment, the gas analysis system of the present invention comprises a laser, where the laser has a longitudinal resonant cavity with an optical axis wherein the ends of the cavity are defined by first and second high reflectivity mirrors; a detector channel having an optical axis, the detector channel optical axis and the laser optical axis defining a first plane; and a gas analysis cell having an optical axis substantially aligned with the laser optical axis, the gas analysis cell positioned within the resonant cavity intermediate the mirrors. The gas analysis cell further comprises an analysis chamber having a first end and a second end; a sample gas inlet port located intermediate the analysis chamber first and second ends for introducing a gas sample into the analysis chamber; first and second buffer gas inlet ports located at the first and second ends of the analysis chamber for introducing a flow of buffer gas into the analysis cell; and first and second outlet ports located at the first and second ends of the analysis chamber, intersecting the first plane and on opposite sides of the optical axis for removing the gases from the analysis cell such that the flow of buffer gas between the buffer gas inlet ports and the outlet ports confines the gas sample to the analysis chamber.

The present invention also provides a method for constraining a gas sample within a gas analysis cell located within a cavity. This method comprises the steps of introducing the gas sample into the analysis cell; forming a first air dam adjacent a first end of the analysis chamber and a second air dam adjacent a second end of the analysis chamber for substantially confining the gas sample within the analysis cell; and forming the first and second air dams so that each has optical characteristics which are substantially the reciprocal of the other so that any steering of a beam of optical radiation propagating through the first air dam is substantially counteracted upon propagation of the beam through the second air dam.

DETAILED DESCRIPTION OF THE INVENTION

Figure 1:
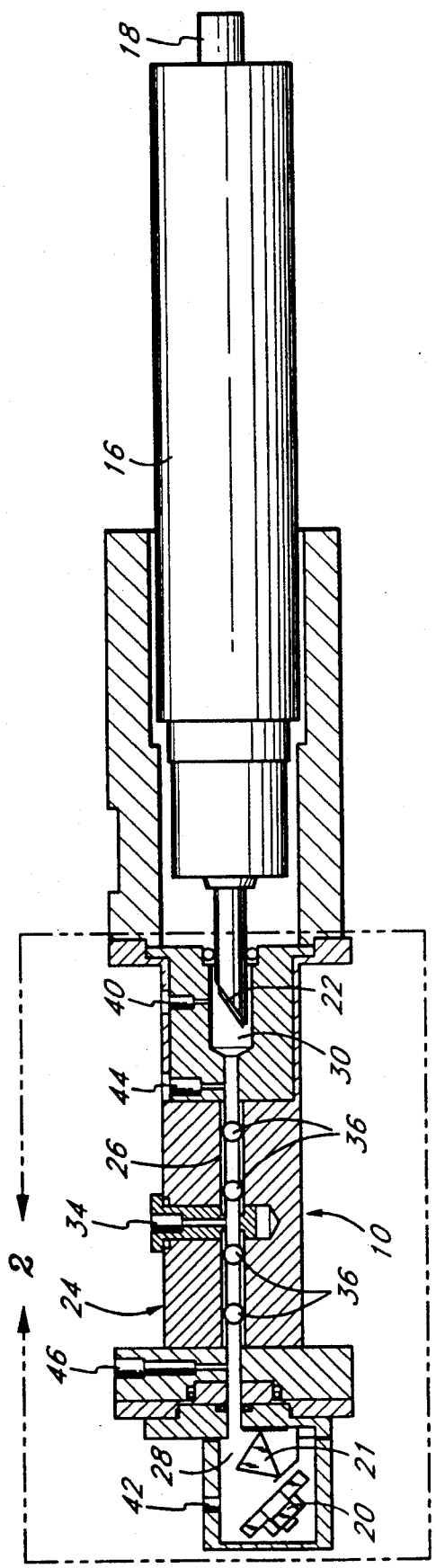
FIG. 1 illustrates a side cross-sectional view of a gas analysis cell within a laser resonant cavity in a gas analysis system in a first embodiment of the present invention.

As shown in FIG. 1, a gas analysis cell 10 in accordance with the present invention is positioned within a resonant cavity of a laser in a gas analysis system. The resonant cavity includes a plasma discharge tube 16 and has a volume which is defined by a first reflector 18 and a second reflector 20. The first reflector 18 preferably comprises a high reflectivity mirror, i.e., a mirror with a reflectivity greater than 99.99%. The reflector 20 preferably comprises a second high reflectivity mirror. Alternatively, the second high reflectivity mirror could be coated on the back side of a Littrow prism. A Brewster prism 21 may be inserted in the cavity to select a particular wavelength of light for circulation through the resonant cavity. A lasing gas mixture is confined within the discharge tube 16 and a Brewster window 22 is positioned at the end of the discharge tube 16 adjacent the output such that the light beam propagating within the cavity enters and exits the discharge tube 16 through the Brewster window 22.

Figure 2:
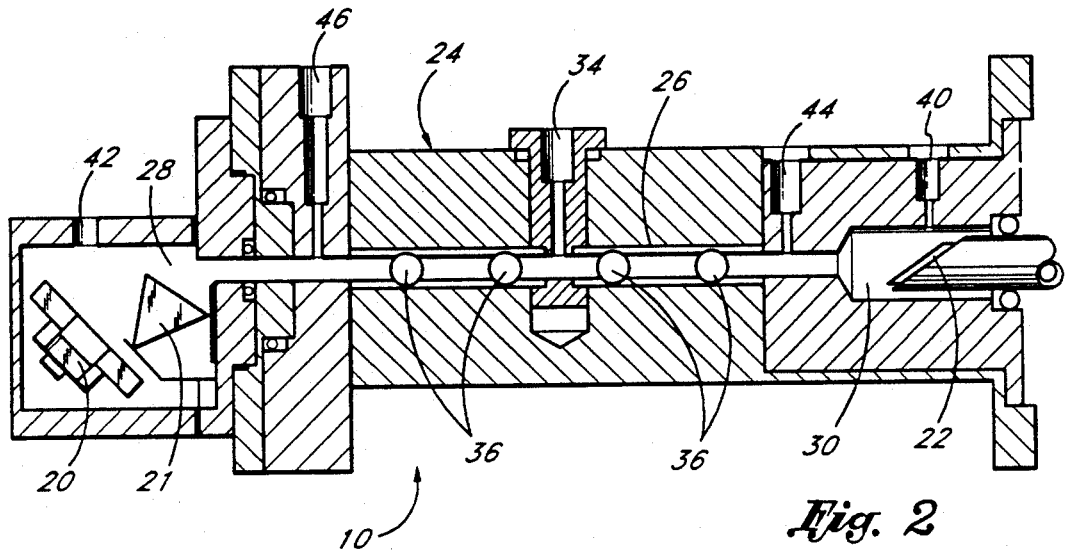
FIG. 2 is an enlarged side cross-sectional view of the gas analysis cell shown in FIG. 1.

Referring to FIG. 1 and FIG. 2, the gas analysis cell 10 is positioned intermediate the Brewster window 22 and second reflector 20 within the laser resonant cavity. The analysis cell 10 comprises a housing 24 enclosing an analysis chamber 26. The analysis cell 10 includes two buffer regions 28, 30 on either end of the analysis chamber 26. The analysis chamber 26 is connected to the source of gas to be analyzed by a gas sample inlet port 34. The gas analysis cell 10 further comprises a plurality of output channels 36 which form optical passageways between the analysis chamber 26 and the outside of the gas cell 10. A first buffer gas input port 40 is connected to the buffer region 30 adjacent the Brewster window 22 and a second buffer gas input port 42 is connected to the buffer region 28 adjacent the second reflector 20. In addition, the cell comprises a first output port 44 connected to the buffer region 30 at the end of the analysis chamber 26 nearest the Brewster window 22. Output port 44 is positioned intermediate the gas sample inlet port 34 and first buffer gas inlet port 40. A second output port 46 is connected to the buffer region 28 at the end of the analysis chamber nearest the second reflector 20. Output port 46 is positioned intermediate the gas sample inlet port 34 and the second buffer gas inlet port 42.

A gas sample which is to be analyzed enters the sampling cell 10 through the input port 34 and is contained within the analysis chamber 26. The laser discharge tube 16 emits a collimated beam of polarized light with a characteristic wavelength dependent upon the type of gas within the discharge tube 16 the orientation of the Brewster prism 21, and the nature of the mirror coating on high reflector mirrors 18,20. The light beam travels an optical path through the Brewster window 22 and through the length of the analysis chamber 26 of the gas analysis cell 10 and is incident upon the second reflector 20. The length of the resonant cavity is such that the light beam resonates between the first and second reflectors 18, 20 which define the volume of the resonant cavity. Thus, the emitted light propagates within the resonant cavity, entering and exiting the discharge tube 16 through the Brewster window 22, thereby stimulating further emission of additional excited atoms within the discharge tube and achieving optimum light amplification. The Brewster prism 21 optimizes the power of a preferred wavelength and polarization state of the laser beam circulating in the resonant cavity. Thus, the Brewster window 22 serves to seal the gas within the discharge tube 16 while also providing polarization control of the light beam by completely transmitting light of a preferred polarization state.

Inside the analysis chamber 26 of the sampling cell 10, the light beam circulating in the resonant cavity intercepts the sample of the gas to be analyzed. The Raman scattered radiation from the gas sample is collected over as large a solid angle as possible by the detector channels 36, which are located approximately perpendicular to and on either side of the axis of the laser light beam propagating inside the analysis chamber 26. The Raman signals can then by analyzed with a microprocessor (not shown) associated with the detector channels 36 and, based on this analysis, the identity and concentration of each specific gas comprising the gas sample contained within the analysis chamber 26 can be determined and reported. A more detailed description of this analysis process can be found in U.S. Pat. No. 4,784,486 entitled "Multi-Channel Molecular Gas Analysis by Laser-Activated Raman Light Scattering", assigned to the assignee of the present invention and incorporated herein by reference.

Figure 2A:
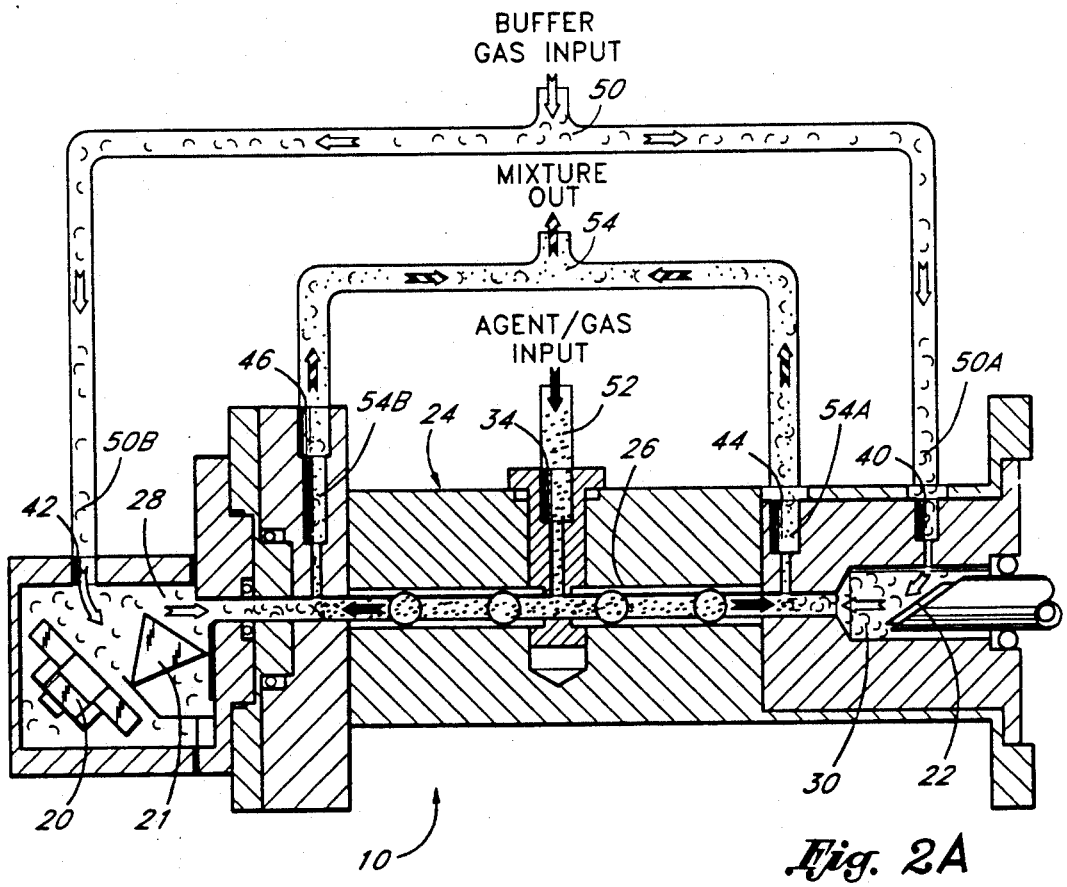
FIG. 2A is an enlarged side cross-sectional view of the gas cell shown in FIG. 2 illustrating the gas flows within the cell.

Referring to FIG. 2A, a flow of buffer gas 50 is introduced into the two buffer gas inlet ports 40, 42 formed in the buffer regions 28, 30 of the cell 10. A portion 50A of the flow 50, input through the first buffer gas inlet port 40, is directed past the Brewster window 22 and toward one end of the analysis chamber 26. A second portion 50B of the flow 50, input through the second buffer gas inlet port 42, is directed past the end reflector 20 and toward the opposing end of the analysis chamber 26. Near the openings in the ends of the analysis chamber 26, the buffer gas flows 50A and 50B mix with the gas sample 52 contained within the analysis chamber 26 and forms gas mixtures 54A and 54B. The gas mixtures 54A and 54B then exit the gas analysis cell 10 through the output ports 44 and 46, respectively, formed in the housing 24 at either end of the analysis chamber 26. Thus, the buffer gas flow 50 through the analysis cell 10 forms a "dam" which constrains the gas sample 52 to the portion of the analysis chamber 26 located intermediate the analysis chamber outlet ports 44, 46. In this manner, the buffer gas flows 50A and 50B serve to protect the optical elements, i.e., the Brewster window 22, the second reflector 20, and the Brewster prism 21, of the gas analysis system from contaminants which may be present in the gas sample 52. This is a significant improvement over typical prior art gas analysis systems in which additional Brewster windows are mounted at each end of the chamber 26 to contain the gas sample 52 within the analysis chamber 26 and protect the remaining optical elements in the cavity from the detrimental effects of the gas sample. Such windows are themselves subject to contamination from the gas sample 52, resulting in laser power losses. Such windows also have intrinsic loss mechanisms which detract from the maximum attainable circulating optical power in the laser resonator. The flow of buffer gas 50A and 50B through the analysis cell 10 eliminates the need for any windows at the ends of the analysis chamber 26, thus maximizing the circulating optical power in the resonant cavity.

In addition to protecting the optics 20, 21, 22 from contaminants in the gas sample 52, the gas analysis cell 10 illustrated in FIG. 1 and FIG. 2 further serves to reduce problems caused by variations in index of refraction and beam steering which often occur as the laser beam propagates through the Brewster window 22. When the laser beam passes through the Brewster window 22 adjacent the discharge tube 16, it is "steered", i.e., deflected, and exits the Brewster window 22 at an angle which is different from the angle at which it entered if the index of refraction of the gases on the two sides of the window are not equal. The angle in reference to the axis of the resonant cavity at which the laser beam emitted from the discharge tube 16 exits the Brewster window 22 is dependent upon 1) The indices of refraction of the window material and the gases on either side of the window; and 2) The angle of the plane in which index of refraction changes occur relative to the axis of the laser beam passing through the analysis cell 10. Note, that if this plane is perpendicular to the beam axis, no change in beam direction will occur regardless of differences in indices of refraction. Obviously, the index of refraction of the window material comprising the Brewster window 22 is fixed. However, the index of refraction of the sample gas on the gas cell side of the window will change as the individual components comprising the gases vary in type and concentration.

With the gas cell 10 of the present invention, the buffer gas flow 50A shown in FIG. 2A immediately in front of the Brewster window 22 along the optical path of the light beam remains constant regardless of what type and concentration of gases comprising the gas sample 52 are introduced into the analysis chamber 26. Since the index of refraction does not change next to the side of the Brewster window 22 adjacent the analysis chamber 26, the angle at which the beam exits the Brewster window is constant and beam steering effects due to the buffer gas are predictable and can be accounted for in the design. One skilled in the art will recognize that the index of refraction of the gas sample 52 contained in the analysis chamber 26 of the gas cell still varies as the concentration of the individual gases comprising the sample varies, and thus, the index of refraction changes where the sample gas mixes with the buffer gas 50 creating the gas mixture 54. If this change in index of refraction occurs in a plane which is nominally perpendicular to the optical path of the laser beam, it will not cause the beam steering problems which occur when the change in refractive index occurs at Brewster window 22, i.e., in a plane which is not perpendicular to the optical path. Furthermore, the buffer gas flow 50 can be utilized not only to prevent beam steering, but also to move unavoidable beam steering effects to a location where the effects are no longer deleterious.

Although the analysis chamber inlet port 34 need not be positioned in the center of the analysis cell as illustrated in FIG. 1 and FIG. 2, there are several advantages associated with this location. When the gas sample 52 is introduced in the center of the gas analysis cell 10, the flow is introduced immediately into the analysis chamber 26 without having to displace the volumes around the optics 20, 22 at either end of the cell. In addition, in analysis systems wherein the gas sample is introduced into one end of the analysis chamber 26, the gas sample flows past each pair of detector channels 36 sequentially. In the analysis cell 10 of the present invention, the gas sample 52 flows into the center of the analysis chamber 26 and then flows away from the inlet 34 in two directions, toward each end of the chamber 26. When input in this manner, two pairs of detector channels 36 are located immediately adjacent to the gas sample input 34, thereby advantageously decreasing response time by as much as one half compared with the response time of prior art systems wherein the gas sample 52 is introduced at one end of the analysis chamber 26.

When the buffer gas flow 50 is input at relatively low flow rates, the flow generally is laminar rather than turbulent in nature. Thus, the point inside the analysis cell 10 at which the gas sample 52 mixes with the buffer gas 50 to form the gas mixture 54 occurs in the laminar flow region, thereby eliminating turbulent mixing and changes in refractive index, i.e., Schlieren effects, which can cause power losses in the transmission of the laser beam.

Figure 3:
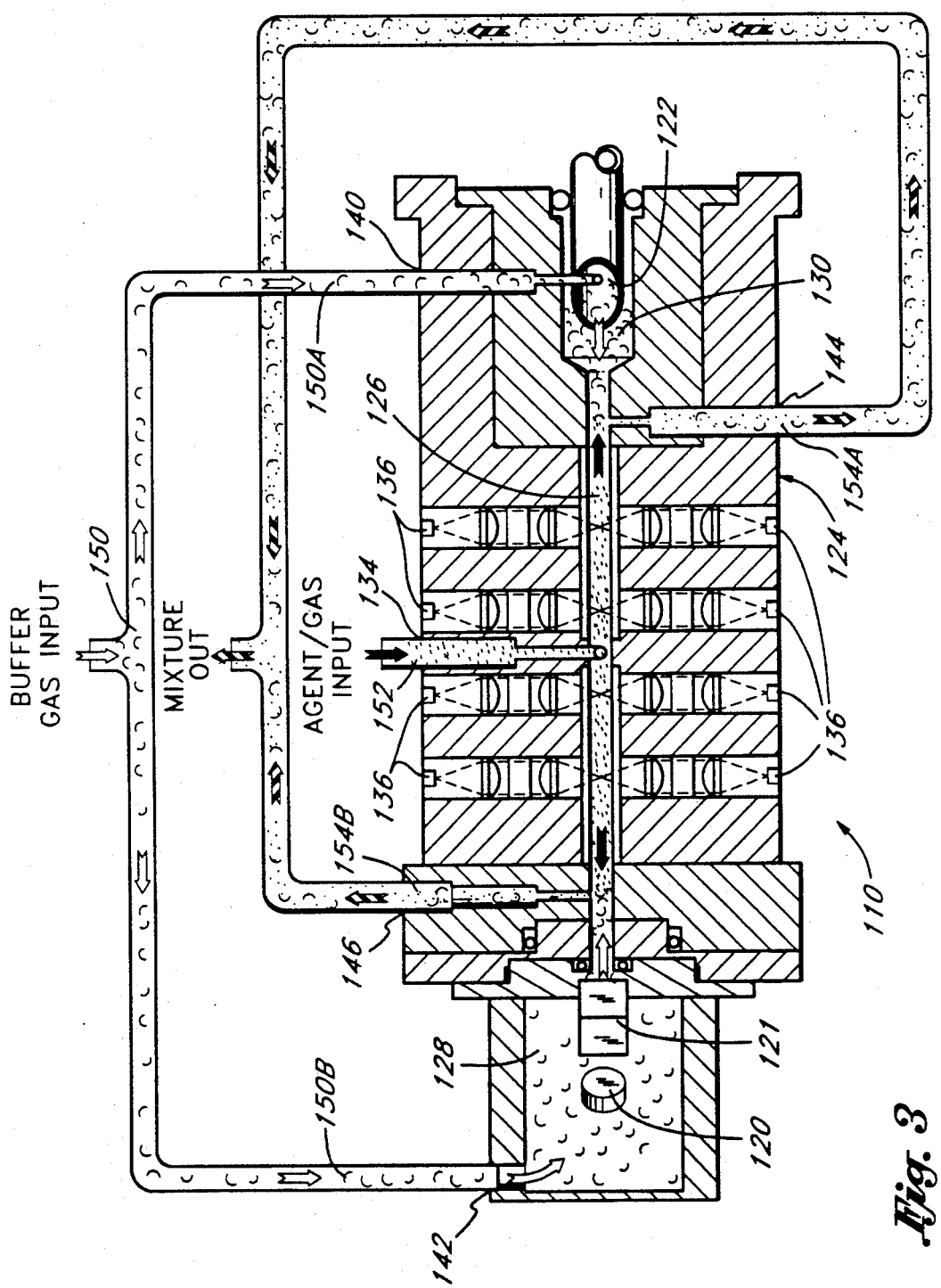
FIG. 3 is a top cross-sectional view of a second embodiment of a gas cell of the present invention illustrating the gas flows within the cell.

FIG. 3 shows a top cross-sectional view of a second embodiment of a gas cell 110 according to the present invention. The analysis cell 110 comprises a housing 124 enclosing an analysis chamber 126. The gas analysis cell 110 is positioned intermediate a Brewster window 122 and second reflector 120 within the laser resonant cavity. The gas cell 110 includes two buffer regions 128, 130 on either end of the analysis chamber 126. The analysis chamber 126 is connected to the source of gas to be analyzed by a gas sample inlet port 134. The gas analysis cell 110 further comprises a plurality of output channels 136 which form optical passageways between the analysis chamber 126 and the outside of the gas cell 110. As shown in FIG. 3, the output channels 136 define an output channel plane which, in the top view shown in FIG. 3, coincides with the plane of the drawing. In FIG. 1, the output channel plane is perpendicular to the plane of the drawing. Referring again to FIG. 3, a first buffer gas input port 140 is connected to the buffer region 130 adjacent the Brewster window 122 and a second buffer gas input port 142 is connected to the buffer region 128 adjacent the second reflector 120. In addition, the cell 110 comprises a first output port 144 connected to the buffer region 130 at the end of the analysis chamber 126 nearest the Brewster window 122. Output port 144 is positioned intermediate the gas sample inlet port 134 and first buffer gas inlet port 140. Additionally, the outlet port 144 has a longitudinal axis which lies in the output channel plane. A second output port 146 is connected to the buffer region 128 at the end of the analysis chamber 126 nearest the second reflector 120. Output port 146 is positioned intermediate the gas sample inlet port 134 and the second buffer gas inlet port 142. Additionally, the outlet port 146 has a longitudinal axis which lies in the output channel plane. Thus, the outlet ports 144 and 146 lie in the same plane. Additionally, in the embodiment shown in FIG. 3, the outlet ports 144 and 146 lie in the output channel plane and on opposite sides of the analysis chamber 126. However, other relative orientations between the plane of the outlet ports 144 and 146 and the plane of the output channels 136 may also be employed.

Referring to FIG. 3, a flow of buffer gas 150 is introduced into the two buffer gas inlet ports 140, 142 formed in the buffer regions 128, 130 of the cell 110. A flow of agent/gas, i.e., analyte gas, 152 is introduced into the analysis chamber 126 via the gas sample inlet port 134. A portion 150A of the flow 150, input through the first buffer gas inlet port 140, is directed past the Brewster window 122 and toward one end of the analysis chamber 126. A second portion 150B of the flow 150, input through the second buffer gas inlet port 142, is directed past the end reflector 120 and toward the opposing end of the analysis chamber 126. Near the openings of outlets 144 and 146 in the ends of the analysis chamber 126, the buffer gas flows 150A and 150B mix with the gas sample 152 contained within the analysis chamber 126 and form gas mixtures 154A and 154B. The gas mixtures 154A and 154B then exit the gas analysis cell 110 through the output ports 144, 146 formed in the housing 124 at either end of the analysis chamber 126. Thus, the buffer gas flow 150 through the analysis cell 110 forms a "dam" which constrains the gas sample 152 to the portion of the analysis chamber 126 located intermediate the analysis chamber outlet ports 144, 146. In this manner, the buffer gas flows 150A and 150B serve to protect the optical elements, i.e., the Brewster window 122, the second reflector 120, and the Brewster prism 121, of the gas analysis system from contaminants which may be present in the gas sample 152. The flow of buffer gas 150A and 150B through the analysis cell 110 eliminates the need for any windows at the ends of the analysis chamber 126, thus maximizing the circulating optical power in the resonant cavity.

In addition to protecting the optics 120, 121 and 122 from contaminants in the gas sample 152, the gas analysis cell 110 illustrated in FIG. 3 further serves to reduce problems caused by variations in index of refraction and beam steering which often occur as the laser beam propagates through the system. Each time the laser beam passes through an optical interface, for example, the Brewster window 122 adjacent the discharge tube 16, it is "steered", i.e., deflected, and exits the Brewster window 122 at an angle which is different from the angle at which it entered if the index of refraction of the gases on the two sides of the window are not equal. The angle in reference to the axis of the resonant cavity at which the laser beam emitted from the discharge tube 16 exits the Brewster window 122 is dependent upon 1) The indices of refraction of the window material and the gases on either side of the window; and 2) The angle of the interface or interfacial region in which index of refraction changes occur relative to the axis of the laser beam passing through the analysis cell 110. If this interface or interfacial region, or any other interface representing a change in index of refraction, is perpendicular to the beam axis, no change in beam direction will occur regardless of differences in indices of refraction. Obviously, the index of refraction of the window material comprising the Brewster window 122 is fixed. However, the index of refraction of the sample gas on the gas cell side of the window will change as the individual components comprising the gases vary in type and concentration.

Figure 4:
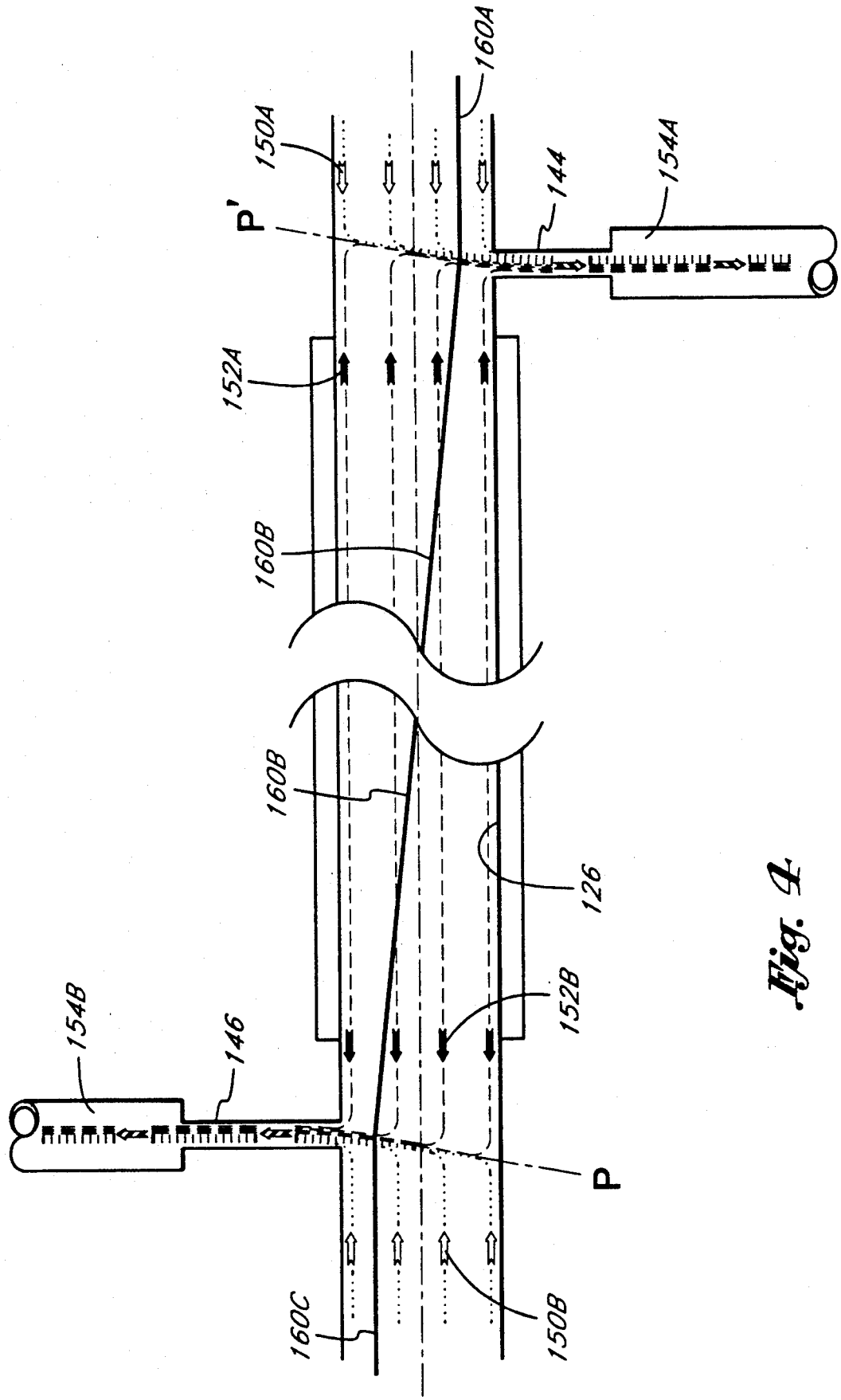
FIG. 4 shows detailed air flow and mixing patterns at the entrance to the outlet ports of the gas cell shown in FIG. 3.

With the gas cell 110 of the present invention, the buffer gas flow 150A shown in FIGS. 3 and 4 immediately in front of the Brewster window 122 along the optical path of the light beam remains constant regardless of what type and concentration of gases comprising the gas sample 152 are introduced into the analysis chamber 126. Since the index of refraction does not change next to the side of the Brewster window 122 adjacent the analysis chamber 126, the angle at which the beam exits the Brewster window is constant and beam steering effects due to the buffer gas are predictable and can be accounted for in the design. One skilled in the art will recognize that the index of refraction of the gas sample 152 contained in the analysis chamber 126 of the gas cell still varies as the concentration of the individual gases comprising the sample varies. Thus, the index of refraction varies in a region surrounding an interfacial region or interface P' (see FIG. 4) formed when sample gas flow 152A and buffer gas flow 150A mix to form the outgoing gas mixture flow 154A. Likewise, the index of refraction varies in a region surrounding an interfacial region or interface P formed when sample gas flow 152B and buffer gas flow 150B mix to form the outgoing gas mixture flow 154B. Thus, due to the mixing of the gases 150 and 152 in the regions proximate to the interfacial regions P and P', there exists an index of refraction profile. For example, if the indices of refraction of the sample gas 152 and buffer gas 150 are not equal, the index of refraction along a path from inside the analysis chamber 126 through interfacial region P to buffer region 128 will define a specific index of refraction profile. Initially, the index of refraction of the profile will be equal to the index of refraction of the sample gas 152. As the path approaches the interfacial region P, crosses the interfacial region P and recedes away from the interfacial region P into the buffer region 128, the index of refraction will vary depending upon the relative concentrations of the sample gas 152 and buffer gas 150 comprising the mixture 154 as well as the magnitude of the difference of the indices of refraction of the sample gas and buffer gas. Once the path is well inside the buffer region 128 the profile will equal the index of refraction of the buffer gas 150. If interfacial regions P and P' are perpendicular to the optical path of the laser beam through the interfacial regions, beam steering does not occur. However, if the interfacial regions P and P' are not perpendicular to the optical path and the indices of refraction of the sample gas 152 and buffer gas 150 are not equal, the previously discussed beam steering may occur.

The embodiment of the invention illustrated in FIGS. 3 and 4 compensates for such beam steering effects by locating the outlet ports 144 and 146 on opposite sides of the gas analysis chamber 126. The effect of locating the outlet ports on opposite sides of the gas analysis chamber is to produce beam steering effects at the interfacial regions P and P' which are substantially equal and opposite (and thus self compensating) when they do occur.

FIG. 4 shows the beam steering that might occur when the air dam buffer gas 150 is air and the analyte gas 152 has a high concentration of nitrous oxide ($N_2O$). In this case, the index of refraction of the analyte gas, $n_A$, is less than the index of refraction of the buffer gas, $n_B$. When a laser beam 160A, traveling from right to left as shown in FIG. 4, passes through the gas interfacial region P', it is bent, i.e., refracted, along a path 160B. The angle between incoming beam 160A and 160B and the offset of beam 160B as it passes through the gas analysis chamber 126 have been exaggerated for clarity. When the beam 160B passes through the second gas interfacial region or interface P, the laser beam is bent, i.e., refracted along a path 160C. If the indices of refraction of buffer gases 150A and 150B are substantially equal and the interfacial regions P and P' are substantially parallel, then the bending of the laser beam at interfacial region P is in a direction which is substantially equal and opposite to the bending of the laser beam at interfacial region P'. Note that if $n_A$ were greater than $n_B$ (instead of less than), then the laser beam 160 would bend in opposite directions. The self compensation would still occur, only in the opposite direction. If $n_A$ and $n_B$ are equal, then no beam bending occurs and the laser beam 160 would follow a straight path through the interfacial regions P and P'.

The amount of beam bending which occurs at each location of mixing defined by interfacial regions P and P' is determined by the angle at which the interfacial regions P and P' make relative to the axis of the laser beam as well as by the magnitude of the difference between the indices of refraction, $n_A$ and $n_B$, of the analyte gas and the buffer gas, respectively. For one bend to be compensated by the other bend, the interfacial regions interface angles at P and P' should be substantially the same.

The interface angles of the interfacial regions P and P' are determined in part by the relative gas flow rates coming from each direction and the geometries of the flow patterns from each direction. In one embodiment, the flow rates of the analyte gas flows 152A and 152B are much greater than the flow rates of the air dam buffer gases 150A and 150B. For example, the flow rate for the analyte gases is in the range of approximately 60 to 120 Ml/min (milli-liters per minute) while the flow rate for the buffer gases is in the range of approximately 4 to 8 Ml/min. The exact flow rates are not as important as the ratio between the two rates. With the above described flow rates, the higher flow rate analyte gas overshoots the outlet ports 144 and 146 somewhat and then turns back towards the outlet ports as shown in FIG. 4. This causes the interface angle between the two gases to tilt in the directions shown by the interfacial regions P and P'.

In order for the laser beam bending which might occur at interfacial region P to be equally compensated for by that which might occur at interfacial region P', the two angles should be substantially equal. This can be achieved if the relative flow rates at each location are substantially the same (assuming the shapes of the flow paths are substantially the same). For the flow rates to be the same, the restrictions in the flow path leading to each location should be substantially equal. This can be accomplished by making the geometries of the gas flow passages leading to the interfacial regions P and P' substantially the same, including, e.g., equal lengths and diameters throughout the system. Alternatively, the air dam buffer gas flows 150A and 150B on each side of the analysis chamber 126 may be independently adjusted.

Adjustment of the angles which interfacial regions P and P' make relative to the laser axis can be individually "tuned" by adjusting the relative analyte flow rates 152A, 152B versus buffer gas flow rates 150A, 150B. In one embodiment, this is accomplished by a needle valve (not shown) located in each of the buffer gas inlet lines 140, 142. Such adjustments of the buffer gas flow rates controls the amount of beam steering which occurs at the interfacial regions P and P' at each end of the gas analysis chamber 126. Control of the flow rates makes it possible to optimize the overall system performance.

Placement of the outlet ports 144 and 146 on opposite sides of the analysis chamber 126 and control of the angles of the interfacial regions P and P' as described above, greatly reduces the heretofore deleterious effects of index of refraction beam steering in a gas analysis system. Thus, the effect of varying index of refraction gases being introduced into the gas cell, such as seen in breath by breath analysis of respiratory gases, have a minimal effect on laser power and hence, overall system performance.

As previously described, in some embodiments of the gas cell 110 the outlet ports 144 and 146, in addition to being located on opposite sides of the cell, are located in the same plane as the detector channels 136 and their associated optics. Due to changes in the index of refraction $n_A$ of the analyte gas, the path of the laser beam through the analysis chamber 126 may change direction somewhat as the analyte gas index of refraction, $n_A$, changes. It will bend one direction or the other as illustrated in FIG. 4, or go straight through without changing if the index of refraction of the analyte gas is the same as that of the buffer gas, depending on the relative indices of refraction of the analyte gases and the buffer gases. This beam movement can have the deleterious effect of causing variations in the amount or intensity of Raman scattered light which reaches the detectors.

Placement of the outlet ports 144 and 146 in substantially the same plane as the detector channels 136 minimizes the effects on detection efficiency caused by laser beam movement within the gas analysis chamber 126. This is because the detector optics which collect the light being scattered from the laser beam by the gas sample are generally focused on a location within the analysis chamber 126 which coincides with the laser beam's nominal location within the chamber 126. When the axis of the laser beam moves in a direction which is perpendicular to the plane of the detector optics, the effect on the intensity of Raman scattered light reaching the detectors is much greater than if the beam movement is in a direction which is parallel to the plane of the detector optics. The effect is similar to looking through a small window. Moving closer to or farther from the window (along the line of sight) does not greatly alter the scene observed. This is to the effect observed by the detectors when the laser beam moves parallel to the detector plane. If, however, one moves past the window in a direction which is perpendicular to the line of sight through the window, the scene can change dramatically depending on the change in the line of sight. This "changing scene" to the eye is analogous to having the intensity of the scattered light signal change at the detector and is what is observed by the detectors when the laser beam moves in a direction which is perpendicular to the plane of the detectors. In most gas analyzer systems, the accuracy of the system depends on the stability and consistency of the intensity of the scattered light signal.

Another embodiment of the present invention combines the features of diametrically opposed outlet ports with placement of the outlet ports in the same plane as the detector channels to optimize both laser performance and detection efficiency.

Although the invention has been described in terms of preferred embodiments, it will be apparent to those skilled in the art that numerous modifications can be made without departing from the spirit and scope of the claims appended hereto. Such modifications are intended to be included within the scope of the claims.

We claim:

1. A gas analysis system comprising:
   a resonant cavity for propagating a beam of optical radiation;
   a gas cell positioned within said resonant cavity and adapted to receive a gas sample in an analysis chamber having an optical axis, said gas cell further comprising a first buffer gas chamber adjacent a first end of said analysis chamber and a second buffer gas chamber adjacent a second end of said analysis chamber, said cell configured to permit said beam of optical radiation to enter and exit said analysis chamber through said first and second buffer gas chambers;
   a first mixed gas outlet port located intermediate said gas analysis chamber and said first buffer gas chamber, wherein sample gases from said analysis chamber mix with buffer gases from said first buffer gas chamber to form a first air dam having a first set of optical characteristics; and
   a second mixed gas outlet port located intermediate said gas analysis chamber and said second buffer gas chamber, wherein sample gases from said analysis chamber mix with buffer gases from said second buffer gas chamber to form a second air dam having a second set of optical characteristics, wherein said second set of optical characteristics are substantially the reciprocal of said first set of optical characteristics so that any steering effects on said beam of optical radiation caused by propagating said beam through said first air dam are substantially reversed so as to counteract said steering effects upon propagation of said beam through said second air dam.

2. A gas analysis system as defined in claim 1 further comprising a detector channel having an optical axis, said detector channel optical axis and said analysis chamber optical axis defining a first plane through said analysis chamber.

3. A gas analysis system as defined in claim 2 wherein said first plane intersects a portion of said first mixed gas outlet port.

4. A gas analysis system as defined in claim 3 wherein said first plane intersects a portion of said second mixed gas outlet port.

5. A gas analysis system as defined in claim 4 wherein said first mixed gas outlet port and said second mixed gas outlet port are located on opposite sides of said analysis chamber optical axis.

6. A gas analysis system as defined in claim 1 wherein said first air dam further comprises an interfacial region formed by said sample gases in said analysis chamber and said buffer gases in said first buffer gas chamber.

7. A gas analysis system as defined in claim 6 wherein said interfacial region is planar.

8. A gas analysis system as defined in claim 6 wherein said interfacial region forms an angle with respect to said analysis chamber optical axis.

9. A gas analysis system as defined in claim 6 wherein said interfacial region is substantially perpendicular to said analysis chamber optical axis.

10. A gas analysis system as defined in claim 1 wherein said first air dam further comprises a region intermediate said sample gases in said analysis chamber and said buffer gases in said first buffer gas chamber, said region having an index of refraction profile which is a function of the indices of refraction of said gas sample and said buffer gas.

11. A gas analysis system comprising:
    a resonant cavity for propagating a beam of optical radiation; and
    a gas cell positioned within said resonant cavity, said gas cell comprising:
    an analysis chamber having an optical axis;
    an inlet port for introducing a gas sample into said analysis chamber; and
    a first air dam adjacent a first end of said analysis chamber and a second air dam adjacent a second end of said analysis chamber for confining said sample gas within said analysis chamber, wherein said beam of optical radiation can enter and exit said analysis chamber through said first and second air dams, said first and second air dams having optical characteristics which are substantially the reciprocal of each other so that any steering of said beam of optical radiation caused by propagating through said first air dam is substantially counteracted upon propagation of said beam through said second air dam.

12. A gas analysis system as defined in claim 11 further comprising a detector channel having an optical axis, said detector channel optical axis and said analysis chamber optical axis defining a first plane through said analysis chamber.

13. A gas analysis system as defined in claim 12 further comprising a first outlet port adjacent said first air dam wherein said first plane intersects a portion of said first outlet port.

14. A gas analysis system as defined in claim 13 further comprising a second outlet port adjacent said second air dam wherein said first plane intersects a portion of said second outlet port.

15. A gas analysis system as defined in claim 14 wherein said first outlet port and said second outlet port are located on opposite sides of said analysis chamber optical axis.

16. A gas analysis system as defined in claim 11 wherein said first air dam further comprises an interfacial region formed by said gas sample in said analysis chamber and buffer gases in a first buffer gas chamber.

17. A gas analysis system as defined in claim 16 wherein said interfacial region is planar.

18. A gas analysis system as defined in claim 16 wherein said interfacial region forms an angle with respect to said analysis chamber optical axis.

19. A gas analysis system as defined in claim 16 wherein said interfacial region is substantially perpendicular to said analysis chamber optical axis.

20. A gas analysis system as defined in claim 11 wherein said first air dam further comprises a region intermediate said gas sample in said analysis chamber and a buffer gas in a first buffer gas chamber, said region having an index of refraction profile which is a function of the indices of refraction of said gas sample and said buffer gas.

21. A gas cell comprising:
an analysis chamber having a sample gas inlet port and an optical axis;
a detector channel having an optical axis, said detector channel optical axis and said analysis chamber optical axis defining a first plane through said analysis chamber;
a first buffer chamber in fluid communication with a first end region of said analysis chamber;
a second buffer chamber in fluid communication with a second end region of said analysis chamber;
a first gas outlet port located intermediate said sample gas inlet port and said first buffer chamber for removing gases from said analysis chamber and said first buffer chamber thereby forming a first mixed gas interfacial region between said analysis chamber and said first buffer chamber, wherein said first plane intersects a portion of said first gas outlet port; and
a second gas outlet port located intermediate said sample gas inlet port and said second buffer chamber for removing gases from said analysis chamber and said second buffer chamber thereby forming a second mixed gas interfacial region between said analysis chamber and said second buffer chamber, wherein said first plane intersects a portion of said second gas outlet port and said first and second gas outlet ports are located on opposite sides of said analysis chamber optical axis.

22. A gas cell as defined in claim 21 wherein said first and second mixed gas interfacial regions have optical properties which are substantially the reciprocal of each other so that any steering of a beam of optical radiation propagating from said first buffer chamber through said first mixed gas interfacial region into said analysis chamber is substantially counteracted upon propagation of said beam of optical radiation propagating from said analysis chamber through said second mixed gas interfacial region into said second buffer chamber.

23. A gas cell as defined in claim 21 wherein said first mixed gas interfacial region is planar.

24. A gas cell as defined in claim 21 wherein said first mixed gas interfacial region forms an angle with respect to said analysis chamber optical axis.

25. A gas cell as defined in claim 21 wherein said first mixed gas interfacial region is substantially perpendicular to said analysis chamber optical axis.

26. A gas cell as defined in claim 21 wherein said first mixed gas interfacial region further comprises a region intermediate said analysis chamber and said first buffer chamber, said region having an index of refraction profile.

27. A gas analysis system comprising:
a laser, said laser having a longitudinal resonant cavity with an optical axis wherein the ends of said cavity are defined by first and second high reflectivity mirrors;
a detector channel having an optical axis, said detector channel optical axis and said laser optical axis defining a first plane; and
a gas analysis cell having an optical axis substantially aligned with said laser optical axis, said gas analysis cell positioned within said resonant cavity intermediate said mirrors, said gas analysis cell comprising:
an analysis chamber having a first second end;
a sample gas inlet port located intermediate said analysis chamber first and second ends for introducing a gas sample into said analysis chamber;
first and second buffer gas inlet ports located at said first and second ends of said analysis chamber for introducing a flow of buffer gas into said analysis cell; and
first and second outlet ports located at said first and second ends of said analysis chamber, intersecting said first plane and on opposite sides of said optical axis for removing said gases from said analysis cell such that the flow of buffer gas between said buffer gas inlet ports and said outlet ports confines said gas sample to said analysis chamber.

28. A method for constraining a gas sample within a gas analysis cell located within a cavity comprising the steps of:
introducing said gas sample into said analysis cell;
forming a first air dam adjacent a first end of said analysis chamber and a second air dam adjacent a second end of said analysis chamber for substantially confining said gas sample within said analysis cell; and
forming said first and second air dams so that each has optical characteristics which are substantially the reciprocal of the other so that any steering of a beam of optical radiation propagating through said first air dam is substantially counteracted upon propagation of said beam through said second air dam.

* * * * *